United States Patent [19]
Herbig et al.

[11] Patent Number: 5,876,752
[45] Date of Patent: Mar. 2, 1999

[54] USE OF INTERFACIALLY-POLYMERIZED MEMBRANES IN DELIVERY DEVICES

[75] Inventors: Scott Max Herbig, Bend, Oreg.; Richard Wilker Korsmeyer, Old Lyme, Conn.; Avinash Govind Thombre, Gales Ferry, Ind.

[73] Assignee: Pfizer Inc., New York, N.Y.

[21] Appl. No.: 969,844

[22] PCT Filed: Aug. 1, 1991

[86] PCT No.: PCT/US91/05337

§ 371 Date: Feb. 3, 1993

§ 102(e) Date: Feb. 3, 1993

[87] PCT Pub. No.: WO92/02212

PCT Pub. Date: Feb. 20, 1992

Related U.S. Application Data

[63] Continuation of Ser. No. 564,008, Aug. 7, 1990, abandoned.

[51] Int. Cl.$^6$ .................................................. A61K 9/36
[52] U.S. Cl. ..................... 424/473; 424/461; 424/464; 424/465; 424/468; 424/480; 424/481; 424/489; 424/499
[58] Field of Search ..................... 424/464, 465, 424/468, 473, 480, 481, 461, 489, 499; 514/960

[56] References Cited

U.S. PATENT DOCUMENTS

| | | | |
|---|---|---|---|
| 3,133,132 | 5/1964 | Loeb et al. | 264/49 |
| 3,270,100 | 8/1966 | Jolkovski et al. | 264/4 |
| 3,538,214 | 11/1970 | Polli et al. | 424/19 |
| 3,577,515 | 5/1971 | Vandegaer . | |
| 3,615,536 | 10/1971 | Williams, Jr. | 430/390 |
| 3,845,770 | 11/1974 | Theeuwes et al. | 128/260 |
| 3,875,074 | 4/1975 | Vassiliades et al. | 252/316 |
| 3,884,801 | 5/1975 | Kesting | 210/23 |
| 3,952,741 | 4/1976 | Baker . | |
| 3,977,404 | 8/1976 | Theeuwes | 424/427 |
| 3,995,631 | 12/1976 | Higuchi et al. . | |
| 4,016,880 | 4/1977 | Theeuwes et al. | 128/260 |
| 4,056,610 | 11/1977 | Barber, Jr. et al. | 424/32 |
| 4,160,020 | 7/1979 | Ayers et al. | 424/15 |
| 4,160,452 | 7/1979 | Theeuwes et al. . | |
| 4,203,439 | 5/1980 | Theeuwes | 128/260 |
| 4,235,236 | 11/1980 | Theeuwes | 128/260 |
| 4,251,387 | 2/1981 | Lim | 252/316 |
| 4,333,972 | 6/1982 | Kesting | 427/244 |
| 4,409,201 | 10/1983 | Heinrich et al. . | |
| 4,423,009 | 12/1983 | Mueller | 428/35 |
| 4,439,196 | 3/1984 | Higuchi | 604/890 |
| 4,455,143 | 6/1984 | Theeuwes et al. . | |
| 4,483,846 | 11/1984 | Koide et al. | 424/19 |
| 4,557,925 | 12/1985 | Lindahl et al. | 424/19 |
| 4,563,212 | 1/1986 | Becher et al. | 71/118 |
| 4,576,604 | 3/1986 | Guittard et al. . | |
| 4,609,374 | 9/1986 | Ayer . | |
| 4,629,619 | 12/1986 | Lindahl et al. | 424/15 |
| 4,629,620 | 12/1986 | Lindahl et al. | 424/15 |
| 4,643,764 | 2/1987 | Scher | 71/100 |
| 4,673,405 | 6/1987 | Guittard et al. | 604/890 |
| 4,687,660 | 8/1987 | Baker et al. | 424/465 |
| 4,693,896 | 9/1987 | Wheatley et al. | 424/480 |
| 4,732,586 | 3/1988 | Dick et al. | 55/158 |
| 4,784,858 | 11/1988 | Ventouras | 424/468 |
| 4,786,500 | 11/1988 | Wong | 424/422 |
| 4,803,076 | 2/1989 | Ranade | 424/438 |
| 4,824,678 | 4/1989 | Lindahl et al. | 424/473 |
| 4,828,705 | 5/1989 | Thakore et al. . | |
| 4,837,111 | 6/1989 | Deters et al. | 424/473 |
| 4,849,457 | 7/1989 | Ichii et al. | 521/62 |
| 4,954,381 | 9/1990 | Cabasso | 428/116 |

FOREIGN PATENT DOCUMENTS

| | | |
|---|---|---|
| 1980276 | 11/1976 | Australia . |
| 1718076 | 3/1978 | Australia . |
| 2255777 | 8/1978 | Australia . |
| 2878077 | 3/1979 | Australia . |
| 3098677 | 5/1979 | Australia . |
| 1785483 | 2/1984 | Australia . |
| 2251183 | 11/1984 | Australia . |
| 5514086 | 10/1986 | Australia . |
| 6532586 | 2/1987 | Australia . |
| 6203386 | 5/1987 | Australia . |
| 6529686 | 5/1987 | Australia . |
| 7071487 | 10/1987 | Australia . |
| 6078086 | 12/1987 | Australia . |
| 7369287 | 12/1987 | Australia . |
| 1252731 | 3/1989 | Canada . |
| 0041210 | 9/1981 | European Pat. Off. . |
| 0056825 | 8/1982 | European Pat. Off. . |
| 0168862 | 1/1986 | European Pat. Off. . |

(List continued on next page.)

OTHER PUBLICATIONS

R. E. Kesting "Synthetic Polymeric Membranes", Wiley–Interscience, 2nd Ed., 1985. (Chapters 3 and 8).
R. E. Kesting "Synthetic Polymeric Membranes", McGraw–Hill, 1971. (Chapters 4 and 5).
R. E. Kesting, "Synthetic Polymeric Membranes", Wiley–Interscience, 2nd Ed., (Chapter 7).
Desalination, vol. 35, pp. 39–58; Amsterdam, Netherlands; H. Strathmann: Development of New Membranes (1980).
Remington's Pharmaceutical Science, pp. 1633–1639 (1988).
Kesting, Robert E. Ph.D. *Synthetic Polymeric Membranes, Porous Membranes* Chapter 4, pp. 84–157 (1985).
Kesting, Robert E. Ph.D. *Synthetic Polymeric Membranes, A Structural Prespective* Chapter 7, pp. 237–286 (1988).
On–Line Printout of World Patents Index Latest; Week 8734; AN 87—239745(34).
Chemical Abstracts, vol. 90, No. 20, May 1979, Abstract No. 153125c, E. Shchori et al.

*Primary Examiner*—Jyothsna Venkat
*Attorney, Agent, or Firm*—Peter C. Richardson; Gregg C. Benson; James T. Jones

[57] ABSTRACT

Devices for controlled release of active substances in the form of tablets, capsules and beads comprised of a porous substructure surrounded by one or more interfacial membranes.

25 Claims, 5 Drawing Sheets

FOREIGN PATENT DOCUMENTS

| | | |
|---|---|---|
| 0171457 | 2/1986 | European Pat. Off. . |
| 0357369 | 7/1990 | European Pat. Off. . |
| 0200386 | 8/1984 | New Zealand . |
| 0192532 | 10/1984 | New Zealand . |
| 0204438 | 5/1985 | New Zealand . |
| 0200519 | 8/1985 | New Zealand . |
| 0214635 | 11/1985 | New Zealand . |
| 0202095 | 5/1986 | New Zealand . |
| 0210310 | 1/1988 | New Zealand . |
| 0217696 | 5/1989 | New Zealand . |
| 0217024 | 7/1989 | New Zealand . |
| 0222107 | 7/1989 | New Zealand . |
| 0218297 | 3/1990 | New Zealand . |

USE OF INTERFACIALLY-POLYMERIZED MEMBRANES IN DELIVERY DEVICES

This is a National Stage filing under 35 USC §371 based on PCT/US91/05337 filed internationally Aug. 1, 1991, and is a continuation of U.S. application Ser. No. 07/564,008 filed Aug. 7, 1990 abandoned.

BACKGROUND OF THE INVENTION

Interfacially-polymerized (IF) membranes which consist of a very thin, dense film are typically coated on a thick porous substrate and are used extensively in the reverse-osmosis desalination of brine. The technology for the formation of economically feasible IF membranes for reverse osmosis was developed by Cadotte et al. and continues to be improved. (Cadotte, J. E., R. S. King, R. J. Majerle, and R. J. Petersen, "Interfacial synthesis in the preparation of reverse osmosis membranes," J. Macromol. Sci.-Chem. A15, 727, 1981)

IF membranes made with siloxanes, alkoxsilyls, or aryloxysilylys have been employed in the separation of gaseous mixtures. (U.S. Pat. No. 4,781,733 "Semipermeable Thin-Film Membranes Comprising Siloxane, Alkoxsilyl, and Aryloxysilyl Oligimers and Copolymers," Bend Research, Inc. Nov. 1, 1989)

IF membranes have also been used to form microcapsules for the controlled release of active ingredients. Several patents have been issued in this area over the past 25 years. A partial list of patented IF microcapsule processes and/or formulations is included in Table 1. Typically these IF microcapsules have been used to facilitate controlled-release pesticide formulations, releasing encapsulated active ingredient by diffusion through the microcapsule walls or by the rupture of the microcapsules.

While the literature is replete with description of tablets, capsules, and multiparticulates which deliver active substances by diffusion or osmotic pumping, none have taught the use of delivering active substances from tablets, capsules, or multiparticulates coated with an IF membrane.

TABLE 1

U.S. Patents Utilizing Interfacially-Polymerized Membranes to Make Microcapsules Patent Number—Company—Patent Title U.S. Pat. No. 3,270,100—Delvan Manufacturing Co. and The Aro Corp.—Method for Making Capsules by Interfacial Polymerization
U.S. Pat. No. 3,577,515—Pennwalt Corp.—Encapsulation by Interfacial Polycondensation
U.S. Pat. No. 3,875,074—Champion International Corp.—Formation of Microcapules by Interfacial Crosslinking of Emulsifier and Microcapsules Produced Thereby
U.S. Pat. No. 4,056,610—Minnesota Mining of Manufacturing Co.—Microcapsule Insecticide Composition; Polyurea Shell, Pyrethroid, Antioxidant, Stabilizer, Solvent, Synergist
U.S. Pat. No. 4,563,212—Monsanto Co.—High Concentration Encapsulation by Interfacial Polycondensation; Microcapsules Containing Agricultural Chemicals
U.S. Pat. No. 4,643,764—Stauffer Chemical Co.—Multiple Types of Microcapsules and Their Production; Polyureas, Polyurethanes Encapsulating Herbicides and Insecticides

SUMMARY OF THE INVENTION

It has now been found that a device for controlled release of one or more active substances into an environment of use, said device comprising a core of said substances, with or without one or more excipients, surrounded by a porous substructure and one or more IF membranes is feasible and practical.

A preferred feature of the device is a membrane to which is permeable and imperforate and where the release is either substantially by osmotic pumping or substantially by diffusion.

A second preferred feature of the device is a membrane which is permeable and perforate and where the release is either substantially by osmotic pumping or substantially by diffusion.

A third preferred feature is a device in which the IF membrane is a polymer such as polyamide, polyurea, polyester, or polyurethane formed by a condensation reaction.

A fourth preferred feature is a device in the form of a tablet, capsule or bead.

A fifth preferred feature is a device having a membrane which is semipermeable and imperforate, where the release is substantially by osmotic pumping and the device is in the form of a capsule, tablet or bead.

The present invention also includes a tablet, capsule or bead for administration to a mammal which releases one or more pharmaceutically active substances into said animal over an appreciable time interval which comprises a core of said active substance or substances, with or without one or more pharmaceutically acceptable excipients, said core being surrounded by a porous substructure and one or more IF membranes.

A preferred feature is a tablet, capsule or bead, wherein the administration is oral and the release is into the fluid of the gastrointestinal tract of said animal.

Preferred is a tablet, capsule or bead wherein the active substance is an antihypertensive agent. Especially preferred are prazosin, nifedipine, trimazosin and doxazosin.

Also preferred is a tablet, capsule or bead wherein the active substance is an antianxiety agent. Especially preferred are hydroxyzine and sertraline.

Also preferred is a tablet, capsule or bead wherein the active substance is an anticlotting agent. Especially preferred is dazmegrel.

Also preferred is a tablet, capsule or bead wherein the active substance is a hypoglycemic agent. Especially preferred is glipizide.

Also preferred is a tablet, capsule or bead wherein the active substance is a cough or cold agent. Especially preferred are brompheniramine, dexbrompheniramine and chlorpheniramine maleates, phenylephrine and pseudoephedrine hydrochlorides and cetirizine.

The present invention also includes a process for preparing a tablet for controlled release of one or more active substances into an environment of use, said tablet comprised of a core of said active substances, with or without one or more excipients, surrounded by one or more IF membranes.

Preferred is a process which comprises the steps of:

a) coating said core with a porous precoat that acts as a substrate for the application of an IF membrane coating, by coating the core with a solution comprised of about 5–20 wt % of a cellulose ester or ethyl cellulose and, optionally, about 0–50 wt % of one or more pore-forming substances such as a mixture of ethanol, butanol, water and glycerol in a suitable solvent, such as acetone, b) air-drying the core coated with the porous precoat, c) immersing the core coated with the porous precoat into an aqueous solution containing an acid scavenger (to prevent the pH from lowering as the polymerization reaction occurs) such as about 0.1–5 wt % triethylamine and polymer reactants such as about 1–15 wt % m-phenylenediamine or polyethyleneimine or phloroglucinol, d) and then, immersing the core, still wet with the aqueous solution, into a hexane solution containing polymer reactants such as 1–15 wt % trimesoyl chloride or toluene diisocyanate and e) drying.

Also part of the present invention is a process for preparing a capsule for controlled release of one or more active substances into an environment of use, said capsule comprised of a core of said active substances, with or without one or more excipients, surrounded by a porous substrate and an IF membrane.

Preferred is a process which comprises the steps of:

a) coating a mandrel device with a porous coating (which functions as a support for an IF membrane coating) by dip-coating the mandrel with a solution comprised of about 5–20 wt % cellulose ester or ethyl cellulose and, optionally, about 0–50 wt % of one or more pore-forming substances such as a mixture of ethanol, butanol, water-and glycerol in a suitable solvent such as acetone, b) air-drying the porous substrate, c) immersing the mandrel device with the porous substrate coating into an aqueous solution containing an acid scavenger such as about 0.1–5 wt % triethylamine and polymer reactants such as about 1–15 wt % m-phenylenediamine or polyethyleneimine or phloroglucinol, d) and then, immersing the mandrel devices with the porous substrate coating, still wet with the aqueous solution, into an organic solution containing polymer reactants such as 1–15 wt % trimesoyl chloride or toluene diisocyanate and e) drying the capsule shell, f) removing the dried capsule shell from the mandrel device, g) filling the capsule with the core material and h) sealing the capsule.

Also part of the present invention is a process for preparing beads for controlled release of one or more active substances into an environment of use, said beads comprised of a core of said active substances, with or without one or more excipients, surrounded by an IF membrane.

Preferred is a process comprising the steps of:

a) spray drying a slurry of said active substances in the form of beads coated with a solution comprised of about 5–20 wt % of a cellulose ester or ethyl cellulose and about 10–50 wt % of one or more pore-forming substances in a suitable solvent such as acetone into a drying chamber to form a porous precoating that serves as a stable support for an IF membrane coating, b) separating the dried beads with the porous precoat from any excess polymer by sieving or by using cyclones, c) mixing the precoated beads into an aqueous solution containing an acid scavenger such as about 0.1–5 wt % triethylamine and a polymer reactant such as about 1–15 wt % m-phenylenediamine, polyethyleneimine, or phloroglucinol, d) and then immediately spraying the slurry into an organic solution consisting of a polymer reactant such as about 1–15 wt % trimesoyl chloride or toluene diisocyanate in hexane, e) separating the beads from the organic solution by sieving or other means and, f) drying.

The present invention also relates to a method for releasing one or more active substances into an environment of use which comprises placing in said environment a device containing said active substances surrounded by an IF membrane.

Preferred in this method is a device which is a tablet, capsule or bead. Especially preferred is said device wherein the membrane is permeable and imperforate or perforate, and the release is substantially either by diffusion or osmotic pumping. Also especially preferred is said device wherein the membrane is semipermeable and imperforate and the release is substantially osmotic pumping.

BRIEF DESCRIPTION OF THE DRAWINGS

Drawing 1 shows the SEM (scanning election microscope) of the porous surface of a tablet precoated with cellulose acetate prior to the application of an interfacial membrane using the procedure of Example 1.

Drawing 2 depicts the release rate of pseudoephedrine from a cellulose acetate coated tablet and a cellulose coated tablet which is further coated with an interfacial membrane (Example 2).

Drawing 3 shows the SEM of the surface of a tablet coated with an interfacial polyamide membrane after release rate tests (Example 2).

Drawing 4 shows the release rate of trimazosin from is a porous cellulose acetate coated tablet and a porous cellulose acetate coated tablet coated further with an interfacial polyamide coating (Example 3).

Drawing 5 shows the release rate of trimazosin from a porous cellulose acetate coated tablet and a porous cellulose acetate coated tablet coated with an interfacial polyurea coating.

DETAILED DESCRIPTION OF THE INVENTION

As previously indicated, an interfacially polymerized (IF) membrane consists of a very thin, dense film which is typically coated on a relatively thick porous substrate. IF membranes are typically formed by a condensation polymerization reaction at the interface between two immiscible phases, each phase containing reactants used to form the polymer film. The substructure can be thick and very porous since its major function is to support the IF membrane coating.

The materials of which IF membranes of the present invention are made typically consist of polyamides, polyureas, polyesters, and polyurethanes. These IF polymeric membranes can be formed from a number of reactant monomers or oligomers. In particular, the following reactants have been used to make IF membrane coatings: m-phenyldiamine, polyethylene imine, phloroglucinol, trimesoyl chloride, and toluene diisocyanate. IF polymer membranes can also be made of other materials and many other reactants can be used to make IF membranes. Essentially all polymers formed by condensation reactions can be formed as IF membranes including those used in reverse osmosis membranes and gas separation membranes. Thus, the list of reactants that can be used to make IF membranes includes any of the reactants used to make the polymer materials used in IF membranes such as ethylenediamine, p-xylylenediamine, sebacyl chloride, hexamethylenediamine, resorcinol, isophthalyl chloride, tetrakis(N-2-aminoethylaminomethyl), tetrakis (aminomethyl)methane, bis(chlorocarbonylalkyl) polysiloxane, bis(aminoalkyl)polysiloxane, epicholohydrin-ethylenediamine copolymer, epiamine, polyetheramine, tri (hydroxoyethyl)isocyanate, furfuryl alcohol, tolylenediamine, 2 nitro p-phenylenediamine, bis(p-aminophenyl)methane, dimethylpiperazine, bis(piperidyl) propane, bis(p-aminophenyl)ether, bis(p-aminophenyl) sulfone, diaminoazobenzene, diaminopyridine, p-aminobenzhydrazide, iso and terephthalicdihydrazide, oxalyldihydrazide, iso and terephthaloylchloride, naphthalenedicarboxylic acid chloride, diphenyldicarboxylic acid chloride, pyridine dicarboxylic acid chloride, fumaroyl chloride, m-benzenedisufonyl chloride, pyromellitic anhydride, bis(p-isocyanatophenyl)methane, isophthaloyl chloride, and piperazine.

The substructure which supports the interfacial membrane consist of cellulose derivatives. In particular, they consist of cellulose esters and ethers, namely, the mono-, di- and triacyl esters wherein the acyl group consists of two to four carbon atoms and lower alkyl ethers of cellulose wherein the alkyl group is of one to four carbon atoms. The cellulose esters can also be mixed esters, such as cellulose acetate butyrate, or a blend of cellulose esters. The same variations can be found in ethers of cellulose and includes blends of cellulose esters and cellulose ethers. Other cellulose derivatives which can be used in making the asymmetric membranes of the present invention include those materials which are associated with reverse osmosis membranes, and include cellulose nitrate, acetaldehyde dimethyl cellulose, cellulose acetate ethyl carbamate, cellulose acetate phthalate, cellulose acetate methyl carbamate, cellulose acetate succinate, cellulose acetate dimethaminoacetate, cellulose acetate ethyl carbonate, cellulose acetate chloroacetate, cellulose acetate ethyl oxalate, cellulose acetate methyl sulfonate, cellulose acetate butyl sulfonate, cellulose acetate p-toluene sulfonate, cellulose cyanoacetates, cellulose acetate trimellitate and cellulose methacrylates. The preferred polymers for the substructure are cellulose esters and cellulose ethers. Especially preferred are cellulose acetate and ethyl cellulose.

These materials can be formed by the acylation of cellulose with the corresponding acyl anhydride or acyl halide. Several of the common cellulose esters are available commercially. Cellulose acetate 394-60, 398-10 and 400-25, having acetyl contents of 39.4, 39.8 and 40%, respectively, are readily available from Eastman Chemical Co., Kingsport, Tenn.

To enhance the porous nature of the substructure a pore-forming substance or substances are dissolved with the cellulose derivative in an appropriate solvent to be applied to the tablet, bead or capsule mandrel. These pore-forming substances are, generally, poor solvents for the cellulose derivatives and evaporate when the coated tablet, bead or capsule mandrel are air dried. The successful formation of a porous substructure requires that the solvent or solvents evaporate more rapidly than the pore-forming substance. In addition, the pore-forming substance must not be a solvent for the polymer.

Other methods for preparing porous substructures can be used, such as those described in EP Application No. 89308716.3 (Publication No. 0357369).

The pore-forming substances are employed to control the porosity of the substructure onto which the interfacial membrane is applied, such that porous channels in the substructure can extend completely through the substructure layer, forming macropores on the surface of the cellulose polymers. Suitable pore-forming substances for this purpose include glycerol, water, alkanols, oils, surfactants, glycols or combinations thereof.

As mentioned, it has now been found that tablets and multiparticulates or beads can be coated with an IF membrane and capsule shells can be made of an IF membrane for release of one or more active substances in an environment of use over a period of time.

The process by which an IF membrane is formed is an interfacial condensation reaction forming a polymer film, Rozelle, L. T., J. E. Cadotte, K. E. Cobian, and C. V. Kopp Jr., "Non-polysaccharide Membranes for Reverse Osmosis: NS-100 Membranes," in Reverse Osmosis and Synthetic Membranes, S. S. Sourivajan (ed.), National Research Council of Canada, Ottawa, Canada (1977), pp. 249–262. In this process polymer-forming reactants are mixed in two immiscible solutions. The condensation polymerization reaction occurs at the interface between the two immiscible solutions, forming a thin film. The film remains thin because the reaction is self-limiting; the reactants in the two immiscible solutions are separated by the thin film, once it forms, preventing additional formation of polymer material and consequently limiting film thickness. In preparing the membrane of the present invention the device is coated with both of the immiscible solutions allowing the IF membrane coating to form at the interface between the two solutions.

Membrane coatings of a cellulose derivative with macropores through the outer skin (perforate membrane coatings) can also be made by adjusting the nature of the porous substrate or processing conditions such as reactant concentrations. Thus, either perforate or imperforate membranes can be formed depending on the porous substrate or processing conditions.

Macropores can also develop in situ by the rupturing of the dense skin located directly over a channel in the substructure. Thus, an imperforate membrane can become perforate during use.

Figure 4:
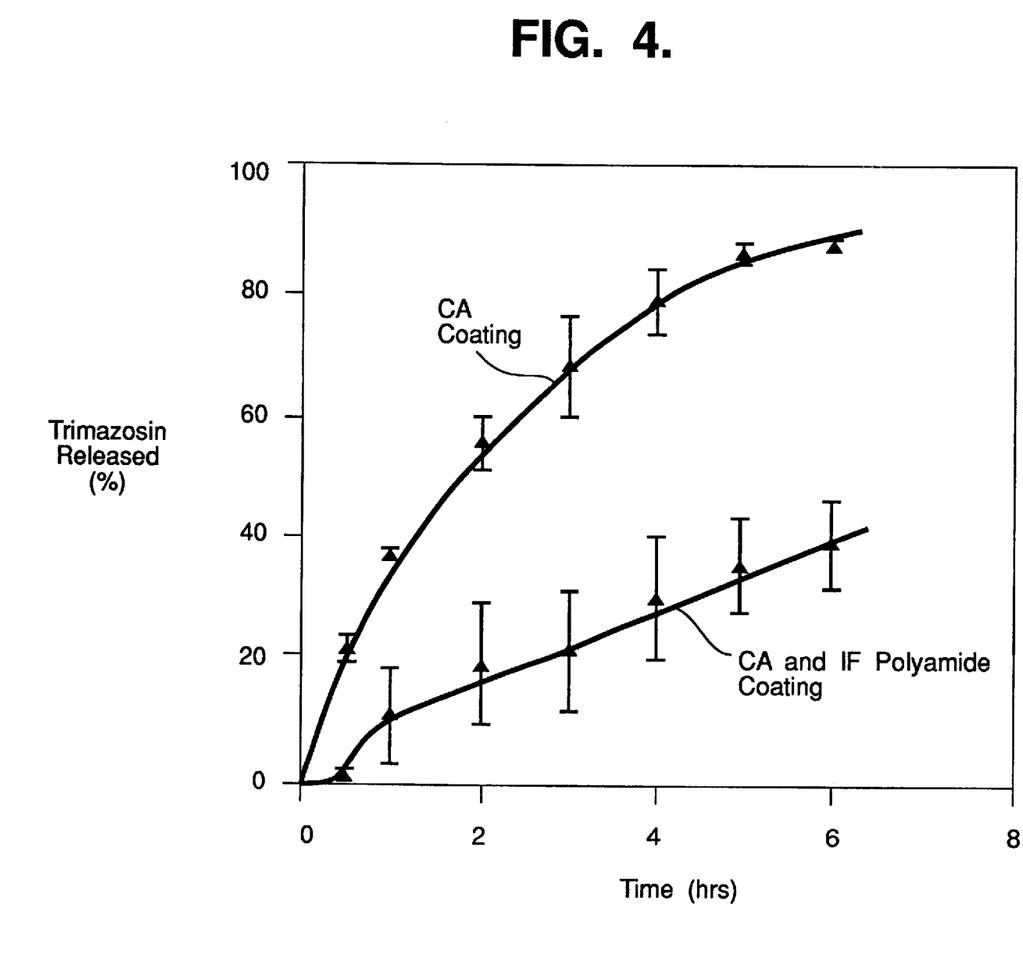

The active substances and excipients are released from the device of the present invention by either diffusion or osmotic pumping or a combination of both (Drawing 4—Example 3). Release by diffusion is a passive phenomenon in which the active substance moves from a region of high concentration (the interior of the device) to a region of lower concentration (the exterior of the device). Release by osmotic pumping makes use of various osmotically effective compounds in the core of the device. These osmotically effective compounds are the driving force of the device and provide a higher osmotic pressure inside the device than that of the exterior environment, which in the case of a medicinal agent being given orally to a human, would be aqueous. Such osmotically effective substances include sugars such as sucrose, lactose, fructose, mannitol and the like; water soluble salts, such as sodium chloride, sodium carbonate, potassium chloride, calcium chloride and sodium sulfate, water soluble acids, alcohols, surfactants and the like. When the device of this invention is intended for human or veterinary use, the osmotic enhancing agents should be pharmaceutically acceptable.

Other excipients present in the devices of this invention include such water soluble binders as polyethylene glycol, gelatin, agar, carboxycellulose, ethylmethylcellulose, polyvinyl alcohol, water soluble starch, polyvinylpyrrolidone and the like; water insoluble binders include cellulose acetate, polyurethane, epoxides and the like. Excipients can include lubricating agents such as magnesium stearate, sodium lauryl sulfate and talc, as well as organic acids and inorganic and organic bases to help solubilize the active substances when released.

The environments of use can vary considerably and include human and animal bodies, soil, plant surfaces, air, aqueous medium and foods and beverages.

Concerning the active substances, these can vary widely in nature; they can be drugs, nutrients, plant growth regulators, fertilizers, biocides, insecticides, pesticides, pheromones, germicides, and such common uses as room deodorizers, pool chlorinators, flavors, fragrances and insect repellents.

When the active substance is a drug, it can be an antihypertensive antianxiety, bronchodilator, hypoglycemic, a cough or cold agent, neoplastic, anti-ulcer, antiinflammatory, hypnotic, sedative, tranquilizer, anesthetic, muscle relaxant, anticonvulsant, antidepressant, antibiotic, analgesic, antiviral, etc. Further such drugs can be in the form of a solution, dispersion, paste, cream, particle, granule, emulsion, suspension or powder.

The shape of the devices of the present invention can also vary greatly. They can be in the form of a tablet, capsule or bead which can be used for the administration of a medicinal agent to a human, or in the case of a capsule, can be sufficiently large to be used as a bolus in administering medicinal agents to ruminants. Further, the tablet can be of sufficient size that it can be used to chlorinate pool water over a sustained period of time, or to deliver large quantities of other active substances.

In summarizing the nature of the membrane of the present devices and the methods for releasing active substances from the core of said device, the membrane can be permeable, meaning that both solvent and active material can pass through the membrane, and imperforate, meaning there are no visible macropores in the membrane. If the membrane is sufficiently strong or the osmotic core pressure sufficiently low, the release from this device may be substantially by diffusion (the term "substantially" implies that most, i.e., over 50% of the release is by this release mechanism). Even if the thin membrane forms macropores, whether or not macropores develop in situ, the device would continue to release by diffusion. If the core of the device contains osmotically effective compounds or substances, the osmotic pressure could result in rupture of the skin over the channels of the substructure and the release will be substantially by osmotic pumping.

The membrane can also be permeable and perforate. The delivery or release without osmotic substances will be substantially by diffusion unless the active substance itself is osmotically active. With osmotic enhancing substances in the core of the device the release can be substantially by osmotic pumping.

The membrane can also be semipermeable, meaning that essentially only the solvent can pass through the membrane, and imperforate. If the pressure within the core of the device is sufficiently high, macropores can develop in situ, as mentioned previously, and the release will be substantially by osmotic pumping.

The rate of release of the active substances from the devices of the present invention can be controlled by the release mechanism, the membrane permeability, the nature of the excipients, the size of the device and the size and number of macropores present in the skin of the membrane. In general, release by osmotic pumping releases the active substances faster than diffusion, all other factors being the same. Excipients which aid in solubilizing the active substance enhance release from the device. Also large and numerous macropores aid in rapid diffusional release of the active substances. In addition, the inherent solubility of the active substance in the solvent of the environment will also affect the rate of release, especially for diffusional drug delivery. Another factor which can influence the rate of release is the thickness of the interfacial membrane and the number of coats of said membrane on the device.

Tablets and beads to be coated with an interfacial membrane are first coated with a 5–20 weight % solution of a cellulose derivative such as cellulose acetate or ethyl cellulose along with 0–50 weight % of a pore-forming substance, if needed, in an appropriate solvent such as acetone. The coated tablet or bead is then air dried to provide the porous substructure on to which is applied the interfacial membrane.

In the case of a capsule, a mandrel is dipped into the above-described solution, withdrawn and allowed to air dry.

The first step in the formation of the interfacial membrane is the immersing of the coated tablet, bead or mandrel into an aqueous solution containing 1–15 weight % of one of the polymer reactants. Preferred are m-phenylenediamine, polyethyleneimine or phloroglucinol.

If the reaction of the two polymer reactants results in the formation of an acid, such as in the reaction of an acid chloride and an alcohol or an amine, it is advantageous to add the aqueous solution of the one reactant a trialkylamine to act as an acid scavenger. The preferred base is triethylamine, and the amount added can be as low as 0.1 weight % and as high as 15 weight %.

The second step in the formation of the interfacial membrane is the treatment of the wet tablet, mandrel or bead with a solution of the second reactant in a suitable solvent such as hexane. The preferred polymer reactants in the organic solution, which are capable of reacting with the first reactants, are trimesolychloride or toluene diisocyanate. Again, the amount of polymer reactant is about 1–15 weight %. The tablet and bead are dried and the coated mandrel is dried and the capsule shell removed, filled with active substance and sealed by conventional means.

A second method for making tablet, beads or capsules coated with an interfacial membrane on a porous substructure involves the combining of the two steps necessary to make the interfacial membrane into one. The tablet, bead or capsule mandrel coated with a porous polymer is immersed or dipped into the two immiscible solvents such as previously described, each containing the requisite polymer reactant, said solvents or solutions being interdiffused by high speed stirring. The time necessary for the formation of the interfacial membrane will vary with the concentration of the polymer reactants. In general, a time of 1–5 minutes is sufficient to allow the reaction to take, place at room temperature.

The treated tablet, bead or capsule mandrel is then dried and treated as previously described.

As the present invention is meant to include capsules in which both tops and bottoms can be composed of interfacial membranes on a porous substructure, it is also meant to include capsules where tops or bottoms can be of some other material, such as gelatin and the other of an interfacial membrane on a porous substructure.

The process for preparing a tablet device surrounded by an IF membrane, is described hereinafter.

As previously indicated, capsules having either the top or bottom made of an asymmetric membrane and the remaining part of an impermeable or semipermeable material is also contemplated by this invention.

It has now been found that an IF membrane can be applied directly to the active substances in the form of a tablet, capsule or bead without the need for a porous substructure.

EXAMPLE 1

Formation of IF Polyamide Tablet Coatings

Figure 1:
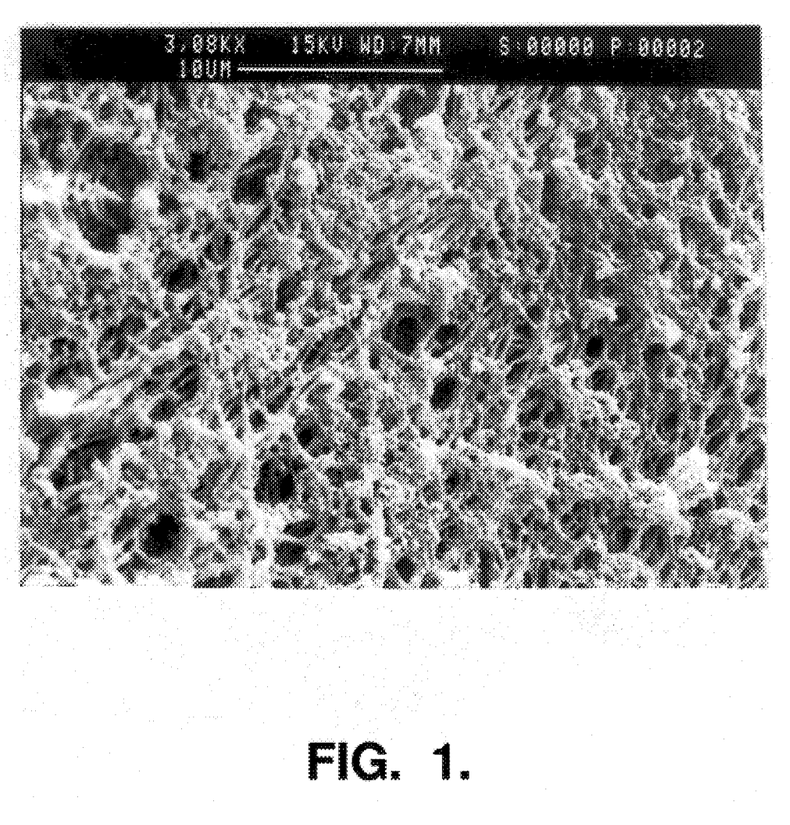

Tablets containing 30 mg of pseudoephedrine hydrochloride (pseudoephedrine) were coated with a porous cellulose acetate precoat to provide a solid support for an interfacially polymerized (IF) coating. The pseudoephedrine tablets were dip-coated by immersing them in a cellulose acetate (CA) coating solution and then withdrawing them slowly (about 5 seconds to completely withdraw a tablet). The coating solution consisted of 5 wt % CA (CA 398-10, Eastman Chemicals, Kingsport, Tenn.), 23 wt % ethanol, 12 wt % butanol, 3 wt % water, and 2 wt % glycerol dissolved in acetone. The tablets were then air-dried at room temperature for at least 4 hours. These precoats were porous, as shown in Drawing 1, and provided a stable support on which the IF coatings could be applied.

IF coatings were applied to the precoated pseudoephedrine tablets by dip-coating the tablets sequentially into an aqueous solution and then into an organic solution. The tablets were first immersed in an aqueous solution containing 4 wt % m-phenylenediamine and 0.5 wt % triethylamine (TEA) and withdrawn slowly. The tablets were then immediately immersed for about 20 seconds into a hexane solution containing 1 wt % trimesoylchloride (TMC). The two reactants, m-phenyldiamine and TMC, formed a polyamide polymer film at the interface between the aqueous coating and the organic coating. The tablets were then air-dried for at least 5 minutes and coated again in the same manner. Five polyamide film coatings were applied in this manner to each tablet to ensure that a leak-free coating was produced. After the fifth IF coating was applied, the coatings were air-dried at room temperature for at least 16 hours. The IF coatings were smooth and continuous and had an overall thickness of less than 2 $\mu$m. (Since the IF coatings were so thin, a supporting precoat was required in this example to ensure that the IF coatings did not lose their integrity during use).

EXAMPLE 2

Sustained Release of Pseudoephedrine from Tablets Coated with IF Polyamide Coatings Pseudoephedrine tablets were coated with a CA precoat and an IF polyamide coating as described in Example 1. The tablets contained 30 mg pseudoephedrine hydrochloride (pseudoephedrine) and had a total weight of 100 mg.

Tablets coated with only the CA precoat and tablets coated with both the CA precoat and an IF polyamide coating were release-rate tested in a buffer solution at 37° C. The buffer solution had an osmotic pressure of 7 atm and consisted of 0.75 wt % potassium chloride, 0.6 wt % boric acid, and sufficient sodium hydroxide to raise the pH to 8.0.

Figure 2:
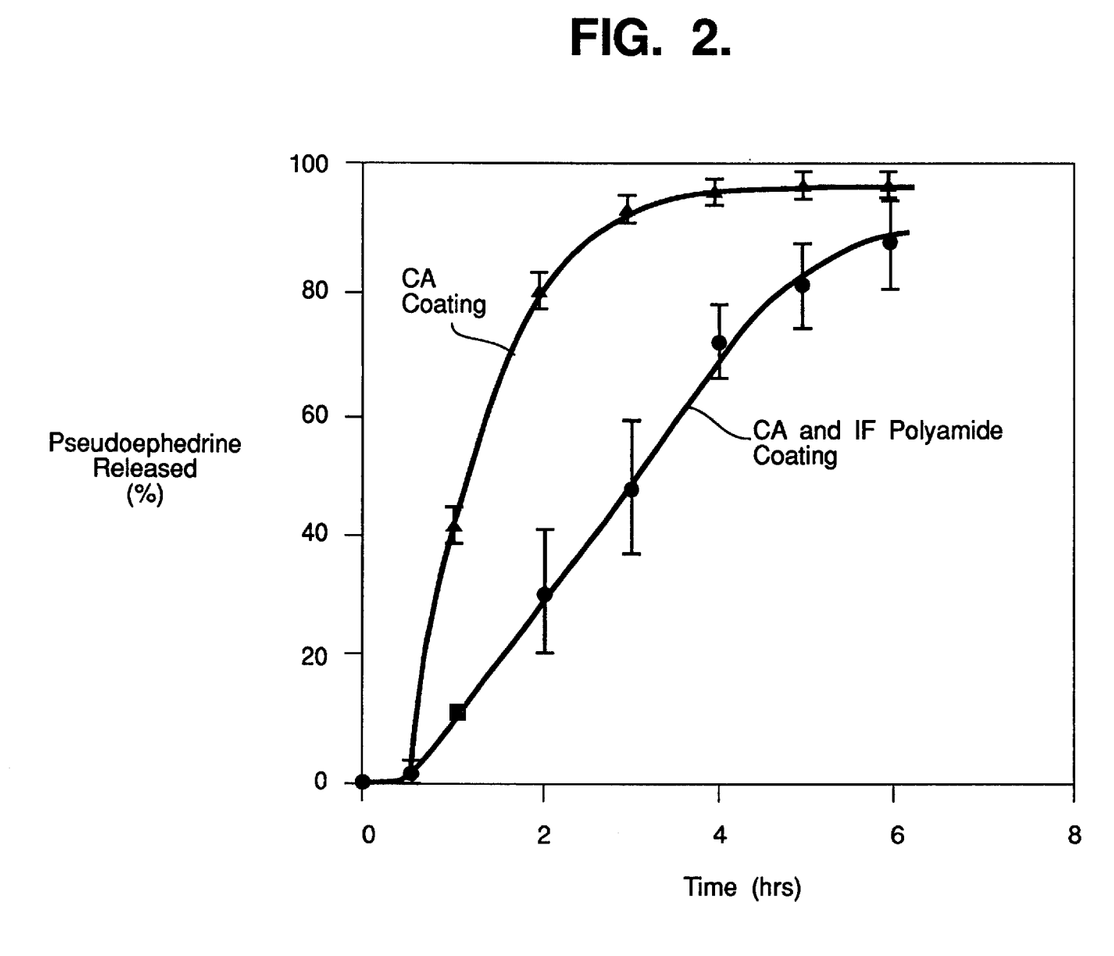

The release rate of pseudoephedrine from the tablets coated with only the CA precoat was over three times the release rate from the tablets coated with the CA precoat and the IF polyamide coating. As shown in Drawing 2, release of pseudoephedrine from the tablets with only the CA precoat followed first-order kinetics (i.e., the release rate continually decreased with time), whereas the release of pseudophedrine was constant from tablets coated with the IF polyamide coating. Approximately 50% of the pseudoephedrine was delivered in about 1 hour from the tablets with the CA precoat, whereas approximately 50% of the pseudoephedrine was delivered in about 3 hours from the tablets with both the CA and IF polyamide coatings. These results indicate that the IF polyamide coating facilitates the sustained release of pseudoephedrine from tablets.

Figure 3:
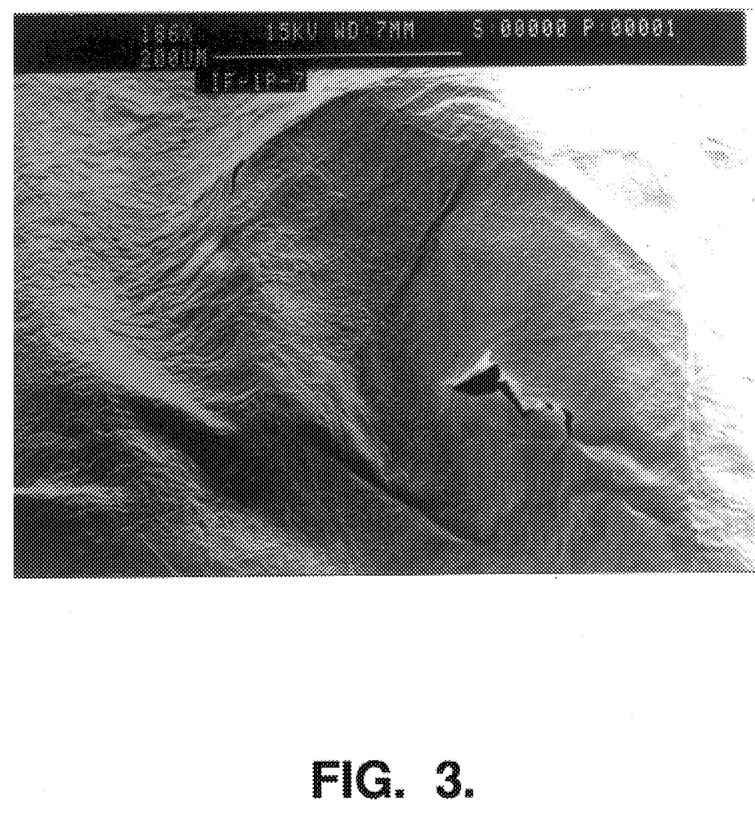

SEM observations after release indicate that the drug was released through small holes and tears formed in the IF polyamide coating. The holes or tears appear to be caused by pressure within the tablet, most likely generated by the osmotic imbibition of water (Drawing 3). Thus, the delivery of pseudoephedrine from tablets coated with an IF polyamide coating was probably facilitated by osmotic pumping of drug solution out of the tablet through the holes or tears. These results also indicate that drug-delivery ports do not need to be incorporated into the IF coating in a separate processing step to facilitate sustained drug release, as is required in commercially available osmotic tablets that utilize dense coatings.

EXAMPLE 3

Sustained Release of Trimazosin from Tablets Coated With IF Polyamide Coatings Trimazosin tablets containing 40 wt % trimazosin, 50 wt % calcium lactate, 9 wt % microcrystalline cellulose (Avicel PH102, FMS Corp., Philadelphia, Pa.), and 1 wt % magnesium stearate, with a total weight of 280 mg, were coated with a porous CA precoat and an IF polyamide coating in the same manner as described in Example 1. The tablets were first coated with a thin film of sucrose to round the sharp edges and provide a smooth substrate for the porous CA precoat.

These tablets were release-rate tested in a 0.06M dextrose solution at 37° C. The dextrose solution had an osmotic pressure of 1.6 atm and a pH of about 7. The release profiles from tablets coated only with the CA precoat and from tablets coated with both the CA precoat and the IF polyamide coating are shown in Drawing 4. Trimazosin was released from the tablets with only the CA precoat much faster than from the tablets with the IF polyamide coating and, unlike the constant rate of release exhibited by the tablets with the IF polyamide coating, exhibited first-order release kinetics (i.e., the release rate was fastest initially and continually slowed with time). These results indicate that the IF polyamide coating facilitated the sustained release of trimazosin and can be used to achieve a constant rate of drug delivery.

EXAMPLE 4

Demonstration of Osmotic Release from Trimazosin Tablets Coated with IF Polyamide Coatings Release rates from tablets described in Example 3 were tested in receptor solutions with different osmotic pressures. The receptor solutions consisted of 0.06M, 0.22M, 0.47M, and 0.94M dextrose solutions which had osmotic pressures of 1.6 atm, 6 atm, 14 atm, and 28 atm, respectively. The trimazosin release rates from the coated tablets into each of the receptor solutions are listed in Table 1. As expected, the release rates decreased as the osmotic pressure of the receptor solution increased. These results indicate that most of the release of trimazosin was due to osmotic delivery. If the trimazosin release had been controlled by diffusion, then the release rates into all of the different receptor solutions would have been the same. In addition to osmotic release there was also a significant contribution of diffusional drug delivery from these tablets, as indicated by the release of trimazosin into the 28-atm receptor solution. The osmotic pressure of a saturated solution of trimazosin and calcium lactate is about 17 atm, so in the 28-atm receptor solution no osmotic driving force existed.

TABLE 1

Trimuzosin Release Rates from Tablets Control With an IF Polyamide Coating Tested in Receptor Solutions With Different Osmotic Pressures

| Osmotic Pressure of Receptor Solution | Release Rate (mg/hr) |
|---|---|
| 1.6 | 4.3 ± 0.7 |
| 6 | 3.2 ± 0.6 |
| 14 | 2.6 ± 0.7 |
| 28 | 1.2 ± 0.2 |

EXAMPLE 5

Formation of IF Polyurea Tablet Coatings

Tablets containing 30 mg pseudoephedrine hydrochloride (pseudoephedrine) were coated with a porous CA precoat, as described in Example 1. IF polyurea coatings were then applied to the precoated tablets by dip-coating the tablets sequentially into an aqueous polyethyleneimine (PEI) solution and then into an organic toluene diisocyanate (TDI) solution. The tablets were immersed in the aqueous solution containing 4 wt % PEI and 0.5 wt % triethylamine and withdrawn slowly. The tablets were then immediately immersed in the hexane solution containing 1 wt % TDI for about 20 seconds. The two reactants, PEI and TDI, formed a polyurea film coating at the interface between the aqueous coating and organic coating. This coating process was repeated 5 times and then the coatings were air-dried at room temperature for at least 70 hours. The IF polyurea coatings were smooth and continuous. The overall thickness of the IF polyurea coatings was about 2 $\mu$m.

EXAMPLE 6

Comparative Osmotically Induced Water Fluxes through IF Films and Dense CA Films Several possible advantages are associated with the use of IF coatings to provide osmotic release of drugs, including increased water flux compared with commercially available dense CA coatings used for osmotic delivery systems. Osmotic release rates are proportional to the water flux through the coating into the drug-containing core. Thus, coatings that facilitate higher water fluxes can facilitate higher release rates and deliver a larger quantity of drugs, especially drugs with low solubilities. Water fluxes for IF films and dense CA films were determined using osmotic test cells. The films were positioned between two compartments, one containing deionized water and the other containing a 0.5 wt % sodium chloride solution. The water flux from the deionized water into the salt solution was measured volumetrically. In addition, the salt flux through the films was measured to ensure that the films did not have leaks. Commercially available IF polyamide films (FT-30, Filmtec Corp., Minneapolis, Minn.) and dense CA films (about 13 $\mu$m thick) cast from a solution consisting of 15 wt % CA (CA 383-40, Eastman Chemicals, Kingsport, Tenn.) dissolved in acetone were tested to determine the osmotic water flux and diffusional salt flux. The salt fluxes through the IF and CA membranes were about 20 $\mu$g/cm2×hr, indicating that neither thin film had significant leaks. The water flux of the IF films (84±7 mg/cm$^2$×hr) was about 50 times greater than that of thin dense CA films (1.6±0.3 mg/cm$^2$×hr). The CA films used in this demonstration were about 8 times thinner than those typically applied to tablets. Thus, tablets coated with IF coatings could have water fluxes several hundred times greater than those of commercial CA coatings. Consequently, these coatings have the potential of providing a much broader range of drug release profiles.

EXAMPLE 7

Sustained Release of Trimazosin from Tablets Coated with IF Polyurea Coatings

Trimazosin tablets were coated with a CA precoat and an IF polyurea coating as described in Example 5. The tablets contained 112 mg trimazosin, 111 mg citric acid, 55 mg sodium citrate, and 2 mg magnesium stearate, for a total weight of 280 mg.

Figure 5:
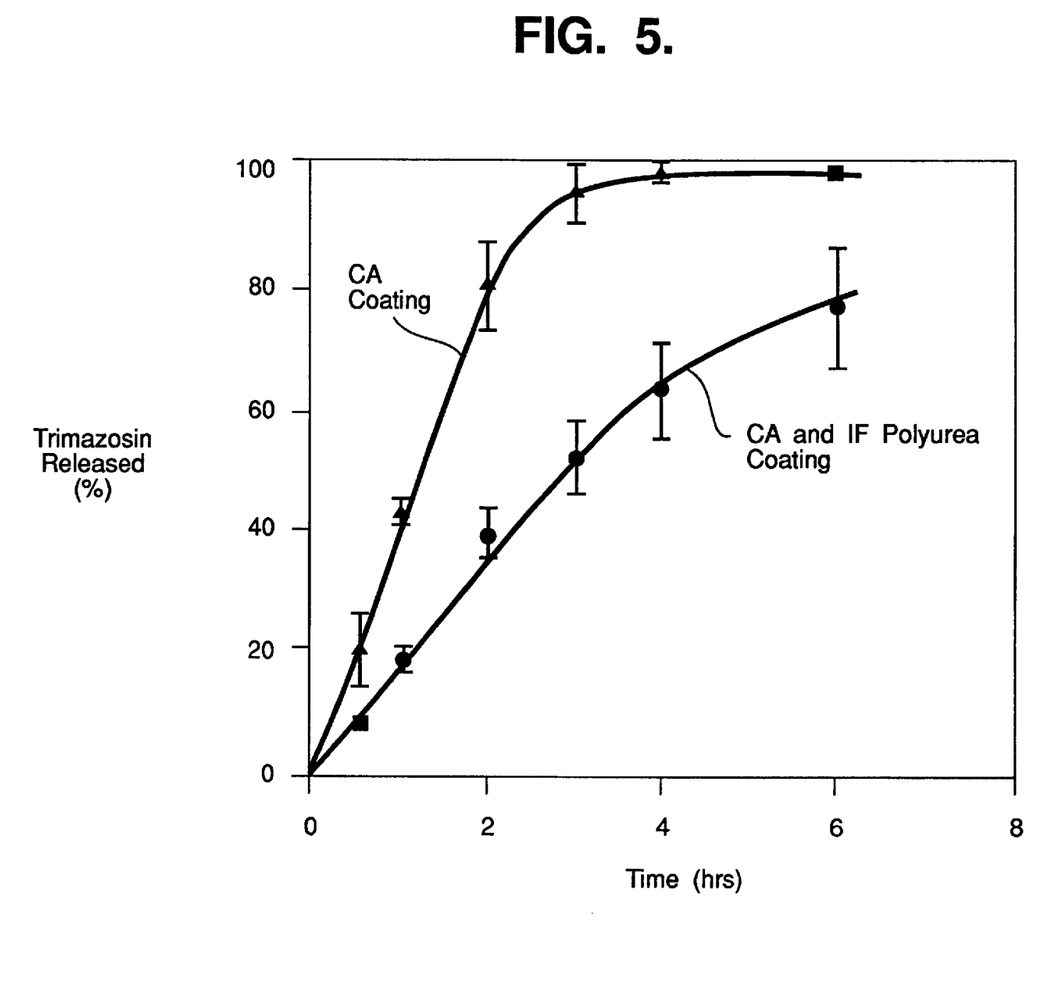

The release rates from tablets coated with only the CA precoat and tablets coated with the CA precoat and an IF polyurea coating were tested in water at 37° C. The release rate of trimazosin from the tablets coated with only the CA precoat was approximately three times the release rate from the tablets coated with the CA precoat and the IF polyurea coating. As shown in Drawing 5, 50% of the trimazosin was released in a little over 1 hour from the tablets with the CA precoat, whereas 50% of the trimazosin was delivered in about 4 hours from the tablets coated with the CA precoat and the IF polyurea coating. These results indicate that the IF polyurea coating facilitates the sustained release of trimazosin from tablets.

EXAMPLE 8

Formation of IF Polyurethane Tablet Coatings

Tablets containing 30 mg of pseudoephedrine hydrochloride (pseudoephedrine) were coated with a porous CA precoat, as described in Example 1. IF polyurethane coatings were then applied to the precoated tablets by dip-coating the tablets sequentially into an aqueous phloroglucinol solution and then into an organic TDI solution. The tablets were immersed in the aqueous solution containing 2 wt % phloroglucinol and 0.5 wt % TEA. The tablets were withdrawn slowly and then immediately immersed in a hexane solution containing 2 wt % TDI for about 20 seconds. The two reactants, phloroglucinol and TDI, formed a polyurethane film coating at the interface between the aqueous coating and the organic coating. This coating process was repeated 5 times for each tablet and then the coatings were air-dried for at least 3 hours. The overall thickness of the IF polyurethane coatings was less than 2 $\mu$m.

EXAMPLE 9

Formation of IF Polyester Tablet Coatings

Tablets containing 30 mg of pseudoephedrine hydrochloride (pseudoephedrine) were coated with a porous CA precoat, as described in Example 1. IF polyester coatings were then applied to the precoated tablets by dip-coating the tablets sequentially into an aqueous phloroglucinol solution and then into an organic TMC solution. The tablets were immersed in the aqueous solution containing 2 wt % phloroglucinol and 0.5 wt % TEA. They were withdrawn slowly and then immediately immersed in a hexane solution containing 2 wt % TMC for about 10 seconds. The two reactants, phloroglucinol and TMC, formed a polyester film coating at the interface between the aqueous coating and the organic coating. This coating process was repeated 5 times for each tablet and then the coatings were air-dried for at least 3 hours. The overall thickness of the IF polyurethane coatings was about 4 µm.

We claim:

1. A device for controlled release of one or more active substances into an environment of use, said device comprising a core of said active substance, with or without one or more excipients, surrounded by a porous substructure consisting of one or more cellulose derivatives, which substructure supports one or more interfacial membranes formed thereon by a condensation reaction, said porous substructure having a composition different from said interfacial membrane.

2. A device of claim 1, wherein the interfacial membrane is permeable and imperforate.

3. A device of claim 1, wherein the interfacial membrane is permeable and perforate.

4. A device of claim 2, wherein the release is substantially osmotic pumping.

5. A device of claim 2, wherein the release is substantially diffusion.

6. A device of claim 3, wherein the release is substantially osmotic pumping.

7. A device of claim 3, wherein the release is substantially diffusion.

8. A device of claim 1, wherein the porous substructure is cellulose ester or ethyl cellulose and the interfacial membrane is a polyamide, polyurea, polyester or polyurethane.

9. A device of claim 1, which is a tablet, capsule or bead.

10. A device of claim 1, wherein the interfacial membrane is semipermeable and imperforate.

11. A device of claim 10, wherein the release is substantially by osmotic pumping.

12. A device of claim 11, which is a capsule, tablet or bead.

13. A tablet, capsule or bead for administration to an animal which releases one or more pharmaceutically active substances into said animal over an appreciable time interval which comprises a core of said pharmaceutically active substances, with or without one or more pharmaceutically acceptable excipients, said core being surrounded by a porous substructure consisting of one or more cellulose derivatives, which substructure supports one or more interfacial membranes formed thereon by a condensation reaction, said porous substructure having a composition different from said interfacial membrane.

14. A tablet, capsule or bead of claim 13, wherein the administration is oral and the release is into the fluid of the gastrointestinal tract of said animal.

15. A tablet, capsule or bead of claim 14, wherein the substance is an antihypertensive selected from the group consisting of prazosin, nifedipine, trimazosin and doxazosin.

16. A tablet, capsule or bead of claim 14, wherein said substance is an antianxiety agent selected from the group consisting of hydroxyzine and sertraline.

17. A tablet, capsule or bead of claim 14, wherein said substance is the anticlotting agent dazmegrel.

18. A tablet, capsule or bead of claim 14, wherein said substance is the hypoglycemic agent glipizide.

19. A tablet, capsule or bead of claim 14, wherein said substance is cough or cold agent selected from the group consisting of brompheniramine, dexbrompheniramine maleate, chlorpheniramine maleate, phenylephrine hydrochloride, pseudoephedrine hydrochloride or cetirizine.

20. A method for releasing one or more active substances into an environment of use which comprises placing in said environment a device containing said active substances surrounded by a porous substructure consisting of one or more cellulose derivatives, which substructure supports an interfacial membrane formed thereon by a condensation reaction, said porous substructure having a composition different from said interfacial membrane.

21. A method of claim 20, wherein the device is a tablet, capsule or bead.

22. A method of claim 20, wherein the interfacial membrane is permeable and imperforate or perforate.

23. A method of claim 22, wherein the release is substantially osmotic pumping.

24. A method of claim 21, wherein the interfacial membrane is semipermeable and imperforate.

25. A method of claim 24, wherein the release is substantially osmotic pumping.

* * * * *